(12) United States Patent
Hu et al.

(10) Patent No.: US 7,191,006 B2
(45) Date of Patent: Mar. 13, 2007

(54) CARDIAC RHYTHM MANAGEMENT SYSTEMS AND METHODS FOR RULE-ILLUSTRATIVE PARAMETER ENTRY

(75) Inventors: Bo Hu, Shoreview, MN (US); Wei Cao, Shoreview, MN (US); Allan T. Koshiol, Lino Lakes, MN (US); James Kalgren, Lino Lakes, MN (US); Paula Dieterle, Champlin, MN (US); Par Lindh, Maple Grove, MN (US); Les Peterson, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 414 days.

(21) Appl. No.: 10/310,702

(22) Filed: Dec. 5, 2002

(65) Prior Publication Data

US 2004/0111131 A1  Jun. 10, 2004

(51) Int. Cl.
*A61B 5/044* (2006.01)
(52) U.S. Cl. ............... 607/30; 607/31; 607/32; 607/59; 607/60; 434/262; 600/523
(58) Field of Classification Search ......... 607/30–32, 607/59–60; 434/262; 600/523; 345/410, 345/440.2, 520
See application file for complete search history.

(56) References Cited

U.S. PATENT DOCUMENTS

| | | | |
|---|---|---|---|
| 4,006,737 A | 2/1977 | Cherry | |
| 4,090,505 A * | 5/1978 | Mortara | 600/515 |
| 4,166,470 A | 9/1979 | Neumann | |
| 4,172,459 A | 10/1979 | Hepp | |
| 4,187,854 A | 2/1980 | Hepp et al. | |
| 4,197,850 A | 4/1980 | Schulman et al. | 128/419 PG |
| 4,208,008 A | 6/1980 | Smith | 371/15 |
| 4,232,679 A | 11/1980 | Schulman | 128/419 PG |
| 4,236,524 A | 12/1980 | Powell et al. | 128/419 PT |
| 4,316,249 A | 2/1982 | Gallant et al. | |
| 4,323,074 A | 4/1982 | Nelms | |
| 4,336,810 A | 6/1982 | Anderson et al. | 128/702 |
| 4,407,288 A | 10/1983 | Langer et al. | 128/419 PG |
| 4,432,360 A | 2/1984 | Mumford et al. | 128/419 PG |

(Continued)

FOREIGN PATENT DOCUMENTS

EP      0565084      10/1993

(Continued)

OTHER PUBLICATIONS

"Screenshots taken of Display of Model 2920 Programmer, Using Model 2845 Software Application", *Guidant Corporation*, 5 pgs, no date.

(Continued)

*Primary Examiner*—Robert E. Pezzuto
*Assistant Examiner*—Deborah Malamud
(74) *Attorney, Agent, or Firm*—Schwegman, Lundberg, Woessner & Kluth, P.A.

(57) ABSTRACT

This document describes systems, devices, and methods for programmably adjusting therapy or other operative parameter values of an implantable cardiac rhythm management device using a programmer that includes a display that graphically illustrates one or more relationship between a parameter being programmed and other parameters and/or rules governing interactions between parameters.

29 Claims, 9 Drawing Sheets

U.S. PATENT DOCUMENTS

| | | | |
|---|---|---|---|
| 4,509,530 A | 4/1985 | Curtis et al. | |
| 4,529,401 A | 7/1985 | Leslie et al. | |
| 4,549,552 A | 10/1985 | Groch et al. | 128/700 |
| 4,680,708 A | 7/1987 | Ambos et al. | 364/417 |
| 4,726,380 A | 2/1988 | Vollmann et al. | |
| 4,809,697 A | 3/1989 | Causey, III et al. | |
| 4,825,869 A | 5/1989 | Sasmor et al. | 128/419 PT |
| 4,947,857 A | 8/1990 | Albert et al. | |
| 4,958,632 A | 9/1990 | Duggan | 128/419 PG |
| 4,969,460 A * | 11/1990 | Callaghan et al. | 607/28 |
| 4,974,598 A | 12/1990 | John | |
| 4,979,506 A * | 12/1990 | Silvian | 607/31 |
| 4,989,610 A | 2/1991 | Patton et al. | |
| 5,000,189 A | 3/1991 | Throne et al. | |
| 5,012,814 A | 5/1991 | Mills et al. | |
| 5,027,824 A | 7/1991 | Dougherty et al. | |
| 5,046,504 A | 9/1991 | Albert et al. | |
| 5,047,930 A | 9/1991 | Martens et al. | 364/413.04 |
| 5,050,612 A | 9/1991 | Matsumura | |
| 5,052,395 A | 10/1991 | Burton et al. | |
| 5,107,850 A | 4/1992 | Olive | |
| 5,113,869 A | 5/1992 | Nappholz et al. | |
| 5,159,926 A * | 11/1992 | Ljungstroem | 607/30 |
| 5,184,614 A | 2/1993 | Collins et al. | 128/419 PG |
| 5,193,550 A | 3/1993 | Duffin | |
| 5,215,083 A | 6/1993 | Drane et al. | 128/419 D |
| 5,224,475 A | 7/1993 | Berg et al. | 128/419 D |
| 5,273,049 A | 12/1993 | Steinhaus et al. | |
| 5,292,341 A | 3/1994 | Snell | |
| 5,299,118 A | 3/1994 | Martens et al. | 364/413.05 |
| 5,309,919 A | 5/1994 | Snell et al. | 128/697 |
| 5,311,873 A | 5/1994 | Savard et al. | |
| 5,311,874 A | 5/1994 | Baumann et al. | |
| 5,312,448 A | 5/1994 | Hognelid et al. | 607/13 |
| 5,315,512 A | 5/1994 | Roth | |
| 5,341,811 A | 8/1994 | Cano | 128/696 |
| 5,342,402 A | 8/1994 | Olson et al. | |
| 5,344,430 A | 9/1994 | Berg et al. | 607/8 |
| 5,360,437 A | 11/1994 | Thompson | |
| 5,371,851 A * | 12/1994 | Pieper et al. | 345/501 |
| 5,379,776 A | 1/1995 | Murphy et al. | |
| 5,404,877 A | 4/1995 | Nolan et al. | 128/671 |
| 5,411,528 A | 5/1995 | Miller et al. | 607/5 |
| 5,421,830 A * | 6/1995 | Epstein et al. | 607/30 |
| 5,423,871 A | 6/1995 | Hoegnelid et al. | 607/28 |
| 5,431,691 A | 7/1995 | Snell et al. | |
| 5,433,198 A | 7/1995 | Desai | 128/642 |
| 5,447,164 A * | 9/1995 | Shaya et al. | 600/523 |
| 5,458,623 A | 10/1995 | Lu et al. | |
| 5,464,433 A | 11/1995 | White et al. | |
| 5,480,422 A | 1/1996 | Ben-Haim | 607/122 |
| 5,487,754 A | 1/1996 | Snell et al. | |
| 5,487,755 A | 1/1996 | Snell et al. | 607/27 |
| 5,496,351 A | 3/1996 | Plicchi et al. | 607/17 |
| 5,507,786 A | 4/1996 | Morgan et al. | 607/27 |
| 5,513,645 A | 5/1996 | Jacobson et al. | 128/710 |
| 5,523,942 A | 6/1996 | Tyler et al. | 364/401 |
| 5,535,753 A | 7/1996 | Petrucelli et al. | |
| 5,549,646 A | 8/1996 | Katz et al. | 607/8 |
| 5,549,654 A | 8/1996 | Powell | |
| 5,555,888 A | 9/1996 | Brewer et al. | |
| 5,578,063 A | 11/1996 | Bocek et al. | |
| 5,584,298 A * | 12/1996 | Kabal | 600/485 |
| 5,603,331 A | 2/1997 | Heemels et al. | |
| 5,607,460 A * | 3/1997 | Kroll et al. | 607/30 |
| 5,609,612 A | 3/1997 | Plicchi et al. | 607/17 |
| 5,613,495 A | 3/1997 | Mills et al. | |
| 5,620,471 A | 4/1997 | Duncan | |
| 5,620,472 A | 4/1997 | Rahbari | 607/27 |
| 5,620,474 A | 4/1997 | Koopman | 607/29 |
| 5,626,620 A | 5/1997 | Kieval et al. | 607/9 |
| 5,626,623 A | 5/1997 | Kieval et al. | 607/23 |
| 5,628,321 A | 5/1997 | Scheib et al. | |
| 5,643,255 A | 7/1997 | Organ | 606/41 |
| 5,647,369 A | 7/1997 | Petrucelli et al. | |
| 5,674,249 A | 10/1997 | de Coriolis et al. | |
| 5,682,489 A * | 10/1997 | Harrow et al. | 715/839 |
| 5,683,431 A | 11/1997 | Wang | 607/28 |
| 5,687,737 A | 11/1997 | Branham et al. | |
| 5,693,075 A | 12/1997 | Plicchi et al. | 607/17 |
| 5,697,959 A | 12/1997 | Poore | |
| 5,713,366 A | 2/1998 | Armstrong et al. | |
| 5,713,937 A * | 2/1998 | Nappholz et al. | 607/30 |
| 5,716,382 A | 2/1998 | Snell | |
| 5,716,383 A | 2/1998 | Kieval et al. | 607/9 |
| 5,716,384 A | 2/1998 | Snell | 607/30 |
| 5,722,999 A | 3/1998 | Snell | 607/32 |
| 5,724,985 A | 3/1998 | Snell et al. | 128/697 |
| 5,725,559 A | 3/1998 | Alt et al. | |
| 5,743,268 A | 4/1998 | Kabal | |
| 5,749,900 A | 5/1998 | Schroeppel et al. | 607/4 |
| 5,749,906 A | 5/1998 | Kieval et al. | 607/9 |
| 5,749,907 A | 5/1998 | Mann | 607/27 |
| 5,755,736 A | 5/1998 | Gillberg et al. | |
| 5,755,742 A | 5/1998 | Schuelke et al. | 607/27 |
| 5,759,199 A | 6/1998 | Snell et al. | 607/60 |
| 5,772,604 A | 6/1998 | Langberg et al. | |
| 5,785,660 A | 7/1998 | van Lake et al. | 600/523 |
| 5,788,640 A | 8/1998 | Peters | |
| 5,792,203 A | 8/1998 | Schroeppel | |
| 5,792,204 A | 8/1998 | Snell | 607/32 |
| 5,803,084 A | 9/1998 | Olson | 128/699 |
| 5,810,740 A | 9/1998 | Paisner | 600/515 |
| 5,814,088 A | 9/1998 | Paul et al. | 607/28 |
| 5,817,137 A | 10/1998 | Kaemmerer | |
| 5,833,623 A | 11/1998 | Mann et al. | 600/523 |
| 5,836,989 A | 11/1998 | Shelton | 607/27 |
| 5,839,989 A | 11/1998 | Saito et al. | 477/143 |
| 5,843,138 A | 12/1998 | Evers et al. | 607/30 |
| 5,876,353 A | 3/1999 | Riff | 600/547 |
| 5,891,043 A | 4/1999 | Ericksen et al. | 600/508 |
| 5,891,178 A * | 4/1999 | Mann et al. | 607/27 |
| 5,891,179 A | 4/1999 | Er et al. | 607/27 |
| 5,897,577 A | 4/1999 | Cinbis et al. | 607/28 |
| 5,908,392 A | 6/1999 | Wilson et al. | 600/509 |
| 5,924,989 A | 7/1999 | Polz | |
| 5,951,484 A * | 9/1999 | Hoium et al. | 600/515 |
| 5,954,664 A | 9/1999 | Seegobin | |
| 5,957,856 A | 9/1999 | Weil et al. | 600/518 |
| 5,957,861 A | 9/1999 | Combs et al. | 600/547 |
| 5,961,467 A | 10/1999 | Shimazu et al. | 600/485 |
| 5,974,341 A * | 10/1999 | Er et al. | 607/31 |
| 5,978,707 A | 11/1999 | Krig et al. | |
| 6,004,020 A | 12/1999 | Bartur | 364/479.06 |
| 6,004,276 A | 12/1999 | Wright et al. | |
| 6,007,493 A | 12/1999 | Ericksen et al. | 600/508 |
| 6,014,581 A | 1/2000 | Whayne et al. | |
| 6,016,442 A | 1/2000 | Hsu et al. | 600/518 |
| 6,016,447 A | 1/2000 | Juran et al. | 607/27 |
| 6,016,448 A | 1/2000 | Busacker et al. | 607/29 |
| 6,017,307 A | 1/2000 | Raines | 600/300 |
| 6,035,233 A | 3/2000 | Schroeppel et al. | 600/515 |
| 6,045,513 A | 4/2000 | Stone et al. | 600/508 |
| 6,073,049 A | 6/2000 | Alt et al. | |
| 6,088,618 A | 7/2000 | Kerver | 607/30 |
| 6,091,990 A | 7/2000 | Hsu et al. | |
| 6,101,415 A | 8/2000 | Er et al. | 607/27 |
| 6,101,416 A | 8/2000 | Sloman | 607/28 |
| 6,151,524 A | 11/2000 | Krig et al. | |
| 6,240,317 B1 | 5/2001 | Villaseca et al. | |
| 6,253,102 B1 | 6/2001 | Hsu et al. | 600/515 |
| 6,289,244 B1 * | 9/2001 | Conley et al. | 607/27 |
| 6,289,248 B1 | 9/2001 | Conley et al. | 607/59 |
| 6,301,503 B1 | 10/2001 | Hsu et al. | |

| | | | |
|---|---|---|---|
| 6,308,100 B1 * | 10/2001 | Er et al. ............... 607/31 |
| 6,308,102 B1 * | 10/2001 | Sieracki et al. ........ 607/59 |
| 6,321,117 B1 | 11/2001 | Koshiol et al. ........ 607/59 |
| 6,400,981 B1 | 6/2002 | Govari ................ 600/509 |
| 6,415,175 B1 | 7/2002 | Conley et al. ........ 600/523 |
| 6,418,340 B1 * | 7/2002 | Conley et al. ........ 600/523 |
| 6,445,952 B1 | 9/2002 | Manrodt et al. ....... 607/28 |
| 6,449,504 B1 * | 9/2002 | Conley et al. ........ 600/523 |
| 6,454,726 B1 | 9/2002 | Catt et al. ............ 600/551 |
| 6,690,972 B2 | 2/2004 | Colney et al. |
| 6,842,644 B2 * | 1/2005 | Anderson et al. ..... 607/32 |
| 7,010,349 B2 | 3/2006 | Conley et al. |
| 2004/0116982 A1 | 6/2004 | Conley et al. |

FOREIGN PATENT DOCUMENTS

WO    WO-99/27992    6/1999

OTHER PUBLICATIONS

US 7,010,348, 03/2006, Koshiol et al. (withdrawn)

* cited by examiner

*FIG. 9B*

CARDIAC RHYTHM MANAGEMENT SYSTEMS AND METHODS FOR RULE-ILLUSTRATIVE PARAMETER ENTRY

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

TECHNICAL FIELD

This document relates generally to medical systems, devices, and methods, and particularly, but not by way of limitation, to cardiac rhythm management systems and methods for rule-illustrative parameter entry.

BACKGROUND

When functioning properly, the human heart maintains its own intrinsic rhythm. Its sinoatrial node generates intrinsic electrical cardiac signals that depolarize the atria, causing atrial heart contractions. Its atrioventricular node then passes the intrinsic cardiac signal to depolarize the ventricles, causing ventricular heart contractions. These intrinsic cardiac signals can be sensed on a surface electrocardiogram (i.e., a "surface ECG signal") obtained from electrodes placed on the patient's skin, or from electrodes implanted within the patient's body (i.e., an "electrogram signal"). The surface ECG and electrogram waveforms, for example, include artifacts associated with atrial depolarizations ("P-waves") and those associated with ventricular depolarizations ("QRS complexes").

A normal heart is capable of pumping adequate blood throughout the body's circulatory system. However, some people have irregular cardiac rhythms, referred to as cardiac arrhythmias. Moreover, some patients have poor spatial coordination of heart contractions. In either case, diminished blood circulation may result. For such patients, a cardiac rhythm management system may be used to improve the rhythm and/or spatial coordination of heart contractions. Such systems often include a cardiac rhythm management device that is implanted in the patient to deliver therapy to the heart.

Cardiac rhythm management systems include, among other things, pacemakers, also referred to as pacers. Pacers deliver timed sequences of low energy electrical stimuli, called pace pulses, to the heart, such as via an intravascular lead wire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly. Such pacers may also coordinate atrial and ventricular contractions to improve pumping efficiency.

Cardiac rhythm management systems also include cardiac resynchronization therapy (CRT) devices for coordinating the spatial nature of heart depolarizations for improving pumping efficiency. For example, a CRT device may deliver appropriately timed pace pulses to different locations of the same heart chamber to better coordinate the contraction of that heart chamber, or the CRT device may deliver appropriately timed pace pulses to different heart chambers to improve the manner in which these different heart chambers contract together.

Cardiac rhythm management systems also include defibrillators that are capable of delivering higher energy electrical stimuli to the heart. Such defibrillators include cardioverters, which typically synchronize the delivery of such stimuli to sensed intrinsic heart activity signals. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering a high energy electrical stimulus that is sometimes referred to as a defibrillation countershock, also referred to simply as a "shock." The shock interrupts the tachyarrhythmia, allowing the heart to reestablish a normal rhythm for the efficient pumping of blood. In addition to pacers, CRT devices, and defibrillators, cardiac rhythm management systems also include devices that combine these functions, as well as monitors, drug delivery devices, and any other implantable or external systems or devices for diagnosing or treating the heart. Cardiac rhythm management systems often include external remote user interfaces (sometimes referred to as "programmers") for programming parameters of an implantable cardiac rhythm management device and/or receiving data telemetered from the implantable cardiac rhythm management device.

One problem faced by cardiac rhythm management systems is in using an external remote user interface to program parameters of the implantable cardiac rhythm management device to tailor the therapy delivered by the implantable cardiac rhythm management device to the needs of the particular subject being treated by that device. Programmable implantable cardiac rhythm management devices often make use of a plethora of programmable parameters. Moreover, such programmable parameters may interact with each other. For example, programming a first parameter to a particular value may limit the range of particular values to which a second parameter may be programmed. Because of this interaction between different programmable parameters, a complex set of rules typically governs how the set of parameters may be programmed. Consequently, a physician faces a daunting task in programming the whole set of parameters to self-consistent values. Moreover, as new therapies are developed (e.g., congestive heart failure therapies that treat both left and right sides of the heart), more parameters and more interactions between parameters are inevitable, further complicating the task of programming a complete set of parameters to allowable values. For these and other reasons, the present inventors have recognized a need for improved techniques for assisting a physician, caregiver, or other user in programming one or more parameters of an implantable cardiac rhythm management device.

BRIEF DESCRIPTION OF THE DRAWINGS

In the drawings, which are offered by way of example, and not by way of limitation, and which are not necessarily drawn to scale, like numerals describe substantially similar components throughout the several views. Like numerals having different letter suffixes represent different instances of substantially similar components.

DETAILED DESCRIPTION

In the following detailed description, reference is made to the accompanying drawings, which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconcilable inconsistencies, the usage in this document controls.

This document discusses, among other things, systems, devices, and methods that will be described in applications involving implantable medical devices including, but not limited to, implantable cardiac rhythm management systems such as pacemakers, cardioverter/defibrillators, pacer/defibrillators, biventricular or other multi-site resynchronization or coordination devices, and drug delivery systems. However, these systems, devices, and methods may be employed in unimplanted devices, including, but not limited to, external pacemakers, cardioverter/defibrillators, pacer/defibrillators, biventricular or other multi-site resynchronization or coordination devices, monitors, programmers and recorders, whether such devices are used for providing a diagnostic, a therapy, or both a diagnostic and a therapy.

Figure 1:
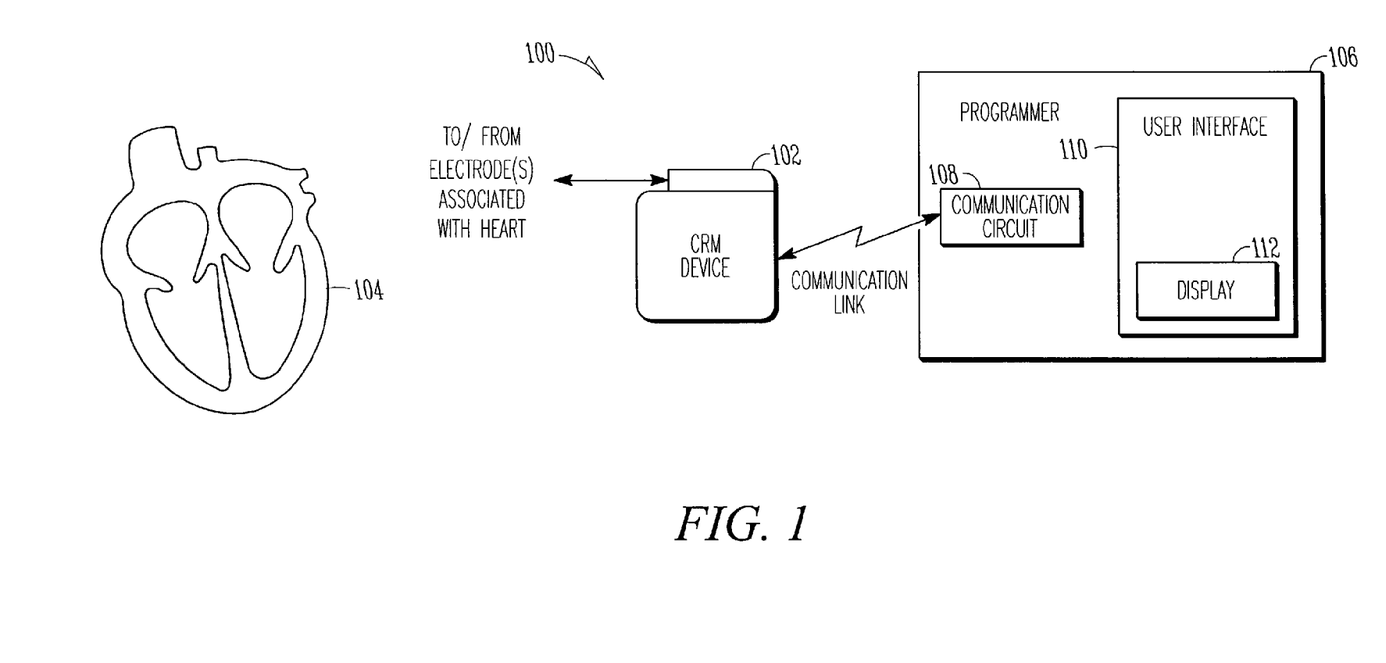
FIG. 1 is a schematic diagram illustrating generally, by way of example, but not by way of limitation, portions of a cardiac rhythm management system.

FIG. 1 is a block diagram illustrating generally portions of a cardiac rhythm management system 100 and portions of an environment in which it is used. In this example, system 100 includes a cardiac rhythm management device 102 coupled to a heart 104 by one or more electrodes associated with heart 104, such as for sensing intrinsic cardiac signals and/or for delivering energy or other therapy to heart 104. System 100 also includes a remote external programmer 106. Programmer 106 includes a telemetry or other communication circuit 108, which is wirelessly or otherwise communicatively coupled to a telemetry or other communication circuit in device 102. Device 102 includes (by way of example, but not by way of limitation) a pacer, a defibrillator, a cardiac resynchronization therapy (CRT) device, a monitor, a device that combines more than one of these functions, or any other implantable or external device for diagnosing and/or treating the heart. In one example, device 102 is sized and shaped for being pectorally or abdominally implanted in a human patient. The electrode(s) coupling device 102 to heart 104 may include an intravascular electrode, an intracardiac electrode, an epicardial electrode, or a housing or a header electrode located on a housing of device 102 or a header attached thereto, or any combination of the above. In some configurations, such as where portion(s) of device 102 are external to the patient, the electrode(s) coupling device 102 to heart 104 may include a skin surface electrode external to the patient. The electrodes may be associated with the heart for bipolar (i.e., two electrodes that are relatively close together) or for unipolar (i.e., two electrodes that are farther apart) signal sensing or therapy energy delivery (e.g., pacing pulse or shocks).

In the illustrative example of FIG. 1, programmer 106 includes a controller or processor that is capable of sequencing through various control states such as, for example, by using a digital microprocessor having executable instructions stored in an associated instruction memory circuit, a microsequencer, or a state machine. The controller or processor typically also includes, or is coupled to, a memory circuit for storing data. Programmer 106 also includes a user input/output interface 110, which includes a display 112. Among other things, a physician or other caregiver (or, in certain cases, the patient) uses user interface 110 for programming therapy and other operative parameters of device 102. As discussed above, such parameters are often subject to a complex set of rules governing how they interact with each other. This often makes the task of programming a consistent set of values for the various parameters extremely difficult for the user. Moreover, because some of these parameters are used for tailoring the particulars of therapy being delivered to the subject, the programming of appropriate values for these parameters is often very important to providing proper therapy to the subject. For these and other reasons, the present inventors have recognized a need for improved techniques for assisting a physician, caregiver, or other user in programming one or more parameters of an implantable cardiac rhythm management device.

Figure 2:
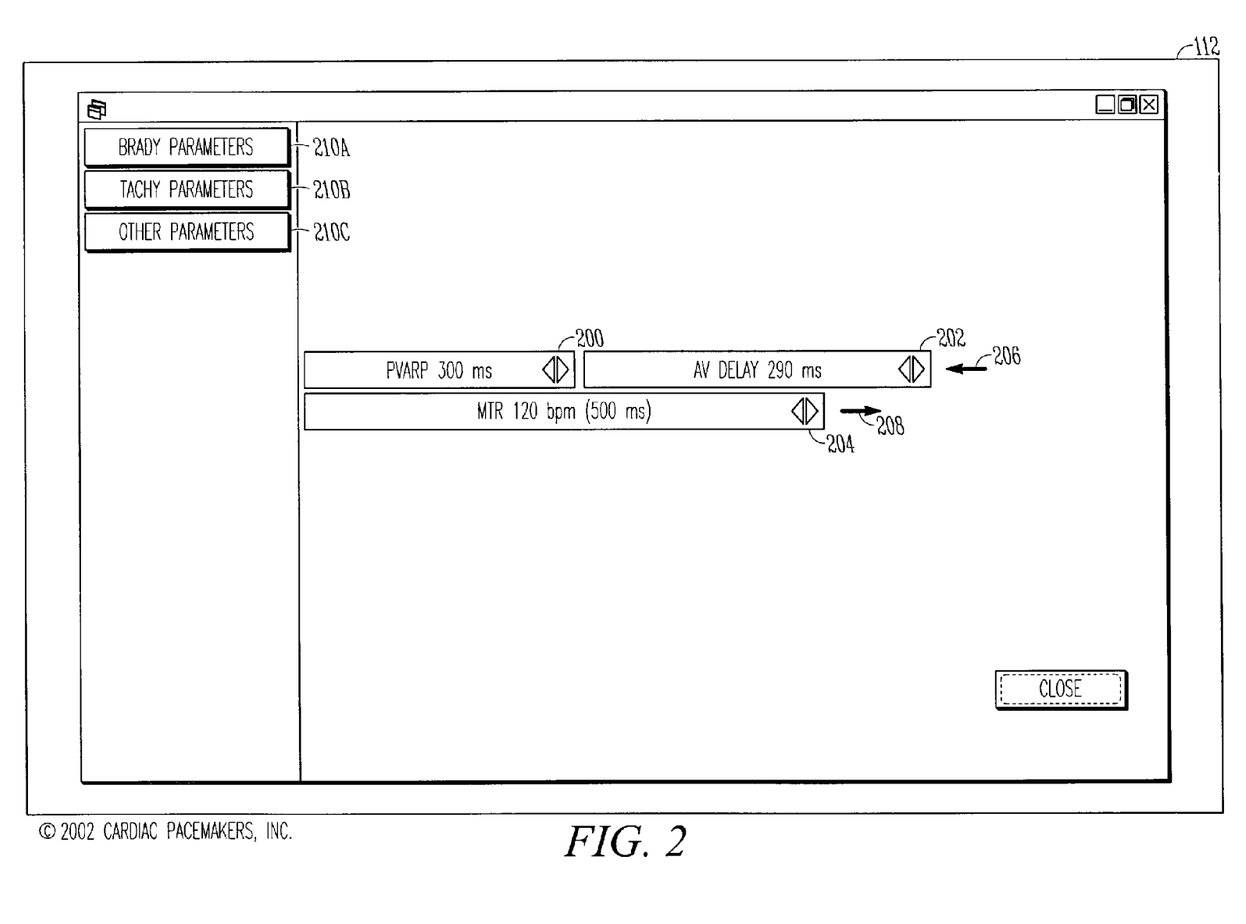
FIG. 2 is a screen shot of a portion of display, including, by way of example, but not by way of limitation, one embodiment of a rule-illustrative system and method for programmably adjusting at least one parameter of a device.

FIG. 2 is a screen shot of a portion of display 112, including, by way of example, but not by way of limitation, one embodiment of a rule-illustrative system and method for programmably adjusting at least one parameter of device 102. In this example, display 112 includes a graphical indication of the at least one parameter to be programmed. In FIG. 2, three cardiac rhythm management therapy parameters are presented: a post-ventricular atrial refractory period (PVARP), a atrio-ventricular (AV) delay, and a maximum tracking rate (MTR). These particular parameters are presented by way of example only, and not by way of limitation. The PVARP defines the length of time ("refractory period") after a paced or sensed ventricular contraction during which any atrial contraction, sensed from an atrial electrode, will be ignored. The AV delay defines a timeout after a paced or sensed atrial contraction after which a ventricular pacing pulse will be delivered if no ventricular contraction has been sensed during the AV delay. The MTR defines a time interval corresponding to a maximum pacing rate, wherein information received from a physiologic sensor is only allowed to drive the patient's pacing rate up to that MTR rate limit.

In this particular example, the graphical indication is presented in the form of a bar graph icon, such as PVARP icon 200, AV delay icon 202, and MTR icon 204. The length of the bar graph icon represents the programmably adjustable value of the corresponding parameter. In the example of FIG. 2, these values are expressed in terms of time intervals, with an optional corresponding indication of rate provided to assist the user in translating between time interval and rate. For example, in FIG. 2, the value represented by PVARP icon 200 is 300 milliseconds, the value represented by AV Delay icon 202 is 290 milliseconds, and the value represented by MTR icon 204 is 500 milliseconds. Additionally, MTR icon 204 also presents the corresponding represented value expressed in terms of rate, i.e., 120 beats per minute (bpm).

In the example of FIG. 2, the parameter icons are "draggable" (e.g., using a computer mouse cursor on display 112, or using a finger on a touch-screen display 112) to change the value of the parameter represented by the icon by dragging an edge of the bar graph parameter icon to increase or decrease its length. In FIG. 2, this is represented by triangles located at an edge of a bar graph icon; the triangles are pointing in opposite directions to indicate to the user that the length of the bar graph parameter icon can be increased or decreased to change the underlying parameter value.

In the example of FIG. 2, the parameter icons are presented in visual correspondence with one another to illustrate to the user a particular rule imposing a limitation on the value of at least one of the parameters. In the example of FIG. 2, the illustrated rule represents a relationship between the allowable time intervals of the PVARP, AV delay, and MTR parameters. More particularly, the rule requires that the sum of PVARP and AV delay not exceed the MTR. This is illustrated by presenting PVARP icon 200 and AV Delay icon 202 side-by-side such that their lengths are additively illustrated, and presenting MTR icon 204, in visual correspondence therewith, such as immediately below PVARP icon 200 and AV Delay icon 202. In this way, the sum of the lengths of PVARP icon 200 and AV Delay icon 202 can be visually compared to the limit imposed by the length of MTR icon 204.

In a further example, a graphical indication flags when the rule has been violated. In one example, a color of the icons and/or the background may change (e.g., from green to red) when a rule violation occurs. In yet a further example, a graphical corrective indication indicates how the rule violation can be corrected. In the example illustrated in FIG. 2, this corrective indication includes arrows 206 and 208. Arrow 206 indicates that the illustrated rule violation can be corrected by decreasing the values of one of PVARP and AV Delay, such that the sum of PVARP and AV Delay no longer exceeds the MTR. Arrow 208 indicates that the illustrated rule violation can alternatively be corrected by increasing the value of MTR such that it exceeds the sum of PVARP and AV Delay.

The rule-illustrative graphical indications, such as illustrated in FIG. 2, make it easier for the user to understand how to program one or more related parameters to particular values that do not violate the illustrated rule governing the relationship between the parameters. FIG. 2 also illustrates icons for organizing therapy and other operative parameters for selection and display by the user. As illustrative examples, FIG. 2 includes "Brady Parameters" icon 210A, "Tachy Parameters" icon 210B, and "Other Parameters" icon 210C. In operation, "clicking" on one of these icons using a mouse cursor triggers a rule-illustrative display of one or more corresponding parameters or, alternatively, a menu for selectively displaying one or more such rule-illustrative parameters.

Figure 3:
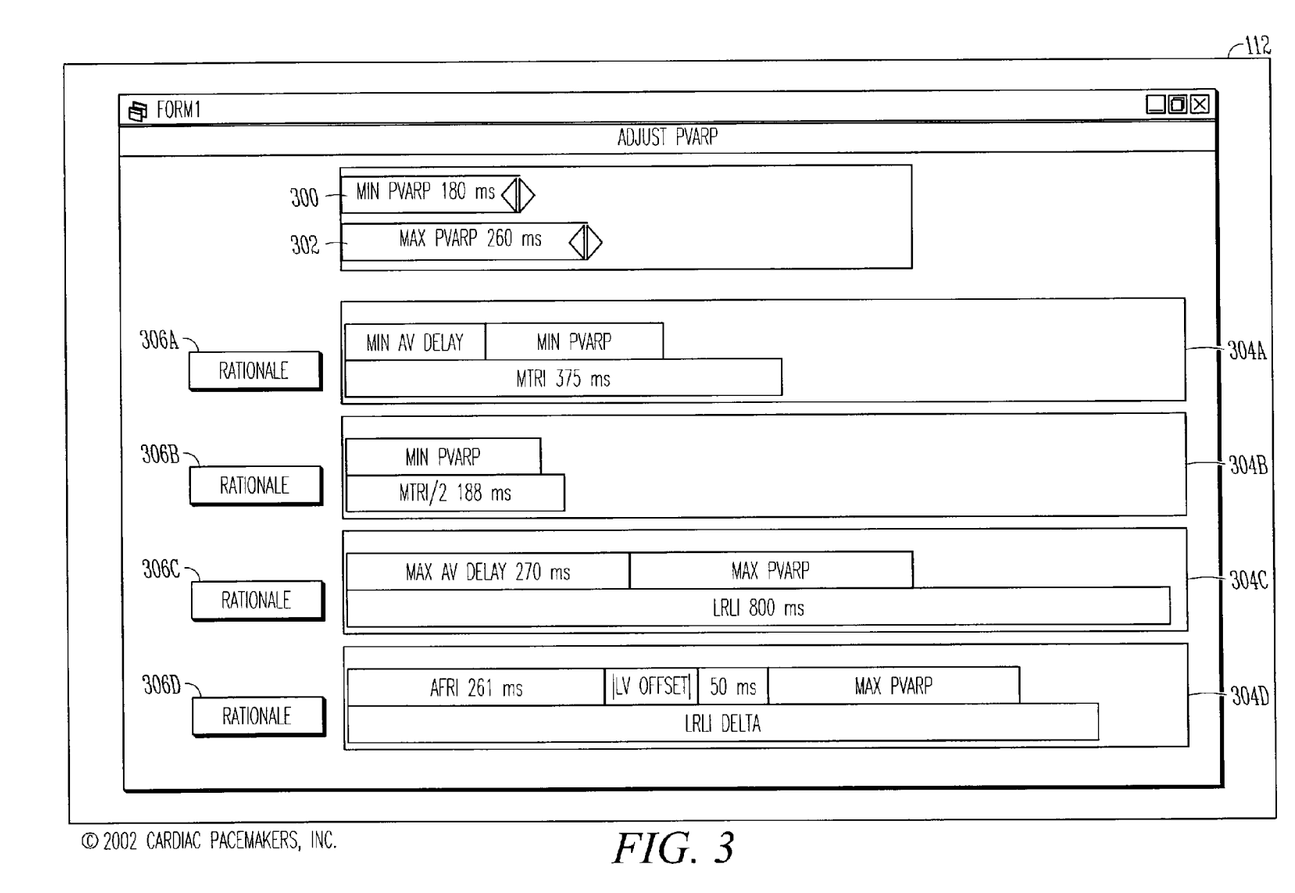
FIG. 3 is a screen shot of an alternative portion of a display, including, by way of example, but not by way of limitation, one embodiment of a rule-illustrative system and method for programmably adjusting at least one parameter of a device.

FIG. 3 is a screen shot of an alternative portion of display 112, including, by way of example, but not by way of limitation, one embodiment of a rule-illustrative system and method for programmably adjusting at least one parameter of device 102. In the example of FIG. 3, display 112 illustrates all rules that are associated with at least one particular parameter being programmed. For example, in FIG. 3, the parameter being programmed in is PVARP, which, in one example, is divided into two sub-parameters, i.e., a minimum PVARP ("Min PVARP") and a maximum PVARP ("Max PVARP"). FIG. 3 is intended to illustrate an example in which display 112 provides a graphical illustration of each rule governing PVARP (i.e., governing Min PVARP or governing Max PVARP). Although FIG. 3 presents an illustrative example of such rules, it is understood that all rules governing the parameter being programmed (e.g., PVARP) need not be displayed concurrently. For example, if the number of rules to be displayed exceeds the available screen space, display 112 provides a scrollbar or other user-accessible device for obtaining or selecting particular rules for display and/or programming.

In the example of FIG. 3, display 112 includes a bar graph Min PVARP icon 300 and a bar graph Max PVARP icon 302, the length of each indicating its value in milliseconds. As discussed above, the user can programmably adjust these values by "dragging" an edge of the Min PVARP icon 300 or the Max PVARP icon 302 to change its length, thereby increasing or decreasing the corresponding parameter value. In this example, display 112 includes four graphical rule indications 304A–D. Each graphical rule indication 304A–D graphically illustrates a rule involving the parameter being programmed (in this case PVARP, which comprises two sub-parameters Min PVARP and Max PVARP). As the user adjusts the length of Min PVARP icon 300 or Max PVARP icon 302, a corresponding length of the same sub-parameter is simultaneously changed in the applicable graphical rule indications 304A–D. This allows the user to visualize how changing a parameter is affected by all the rules related to that parameter. It further enables the user to visualize which rule is violated, if any, how close other rules are to being violated, which other parameters affect those rules, and how the values of those other parameters could be adjusted to avoid violation of one or more rules.

For example, graphical rule indication 304A indicates a rule in which the sum of a Minimum AV Delay ("Min AV Delay") parameter and Min PVARP must not exceed the Maximum Tracking Rate Interval (MTRI). Graphical rule indication 304B indicates a rule in which the Min PVARP must not exceed ½ of the MTRI. Graphical rule indication 304C indicates a rule in which the sum of a maximum AV Delay ("Max AV Delay") and Max PVARP must not exceed a Lower Rate Limit Interval (LRLI). Graphical rule indication 304D indicates a rule in which the sum of an Atrial Fibrillation Rate Interval (AFRI), a Left Ventricular Offset (LV Offset), and a 50 millisecond constant must not exceed a difference between LRLI and a margin parameter ("Delta").

Figure 4:
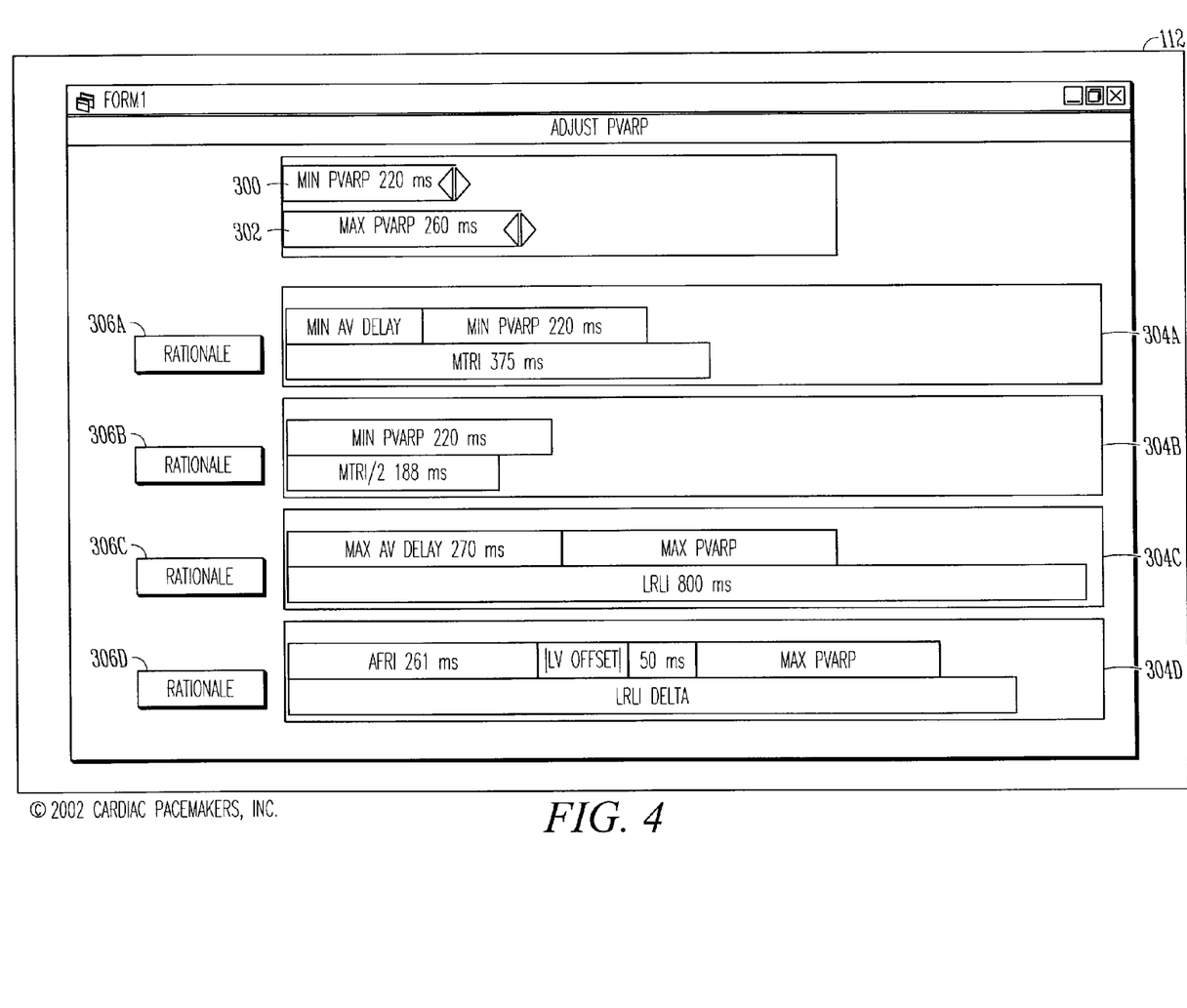
FIG. 4 illustrates the screen shot of FIG. 3 in which a first rule violation is flagged.

In the example of FIG. 4, the user has dragged the edge of the Min PVARP icon 300 to increase its value from 180 milliseconds to 220 milliseconds. As a result, the second illustrated rule (indicated by graphical rule indication 304B) has been violated since Min PVARP now exceeds MTRI/2. In response to this rule violation, the background of graphical rule indication 304B has changed shading or color (e.g., from white to yellow).

Figure 5:
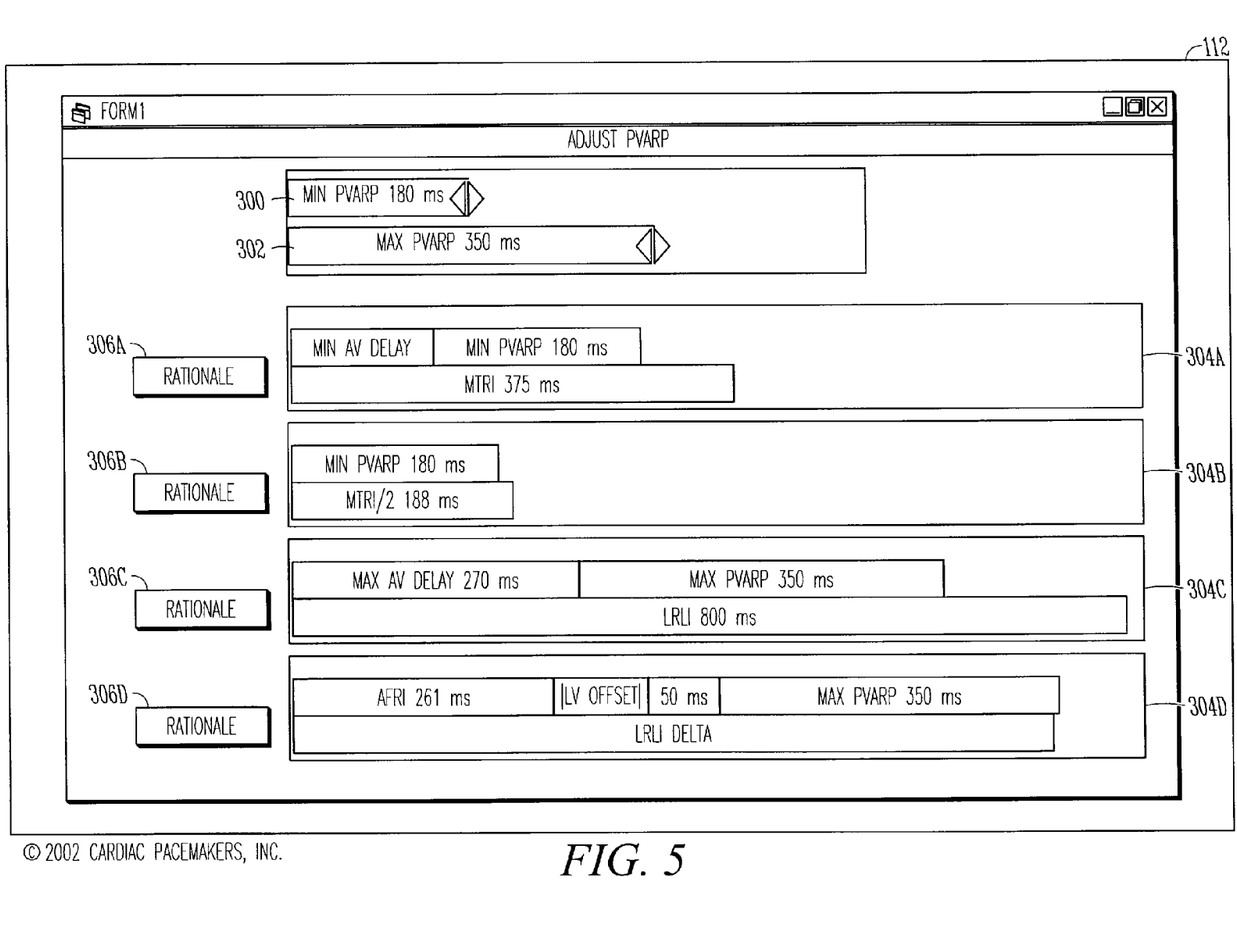
FIG. 5 illustrates the screen shot of FIG. 3 in which a second rule violation is flagged.

In the example of FIG. 5, the user has dragged the edge of the Max PVARP icon 302 to increase its value from 260 milliseconds to 350 milliseconds. As a result, the fourth illustrated rule (indicated by graphical rule indication 304D) has been violated since the sum of AFRI, LV Offset, a 50 millisecond constant, and Max PVARP now exceeds the limit imposed by LRLI—Delta, illustrated immediately below that sum. In response to this rule violation, the background of graphical rule indication 304D has changed shading or color (e.g., from white to red). In one example, different colors of changed shading in response to a rule violation convey different information. For example, a changed background shading from white to yellow may indicate violation of a recommended rule, whereas a changed background from white to red may indicate violation of an absolute rule. In one example, a user is allowed to program a combination of parameter values that violates a recommended rule, but is not allowed to program a combination of parameter values that violates an absolute rule.

Figure 6:
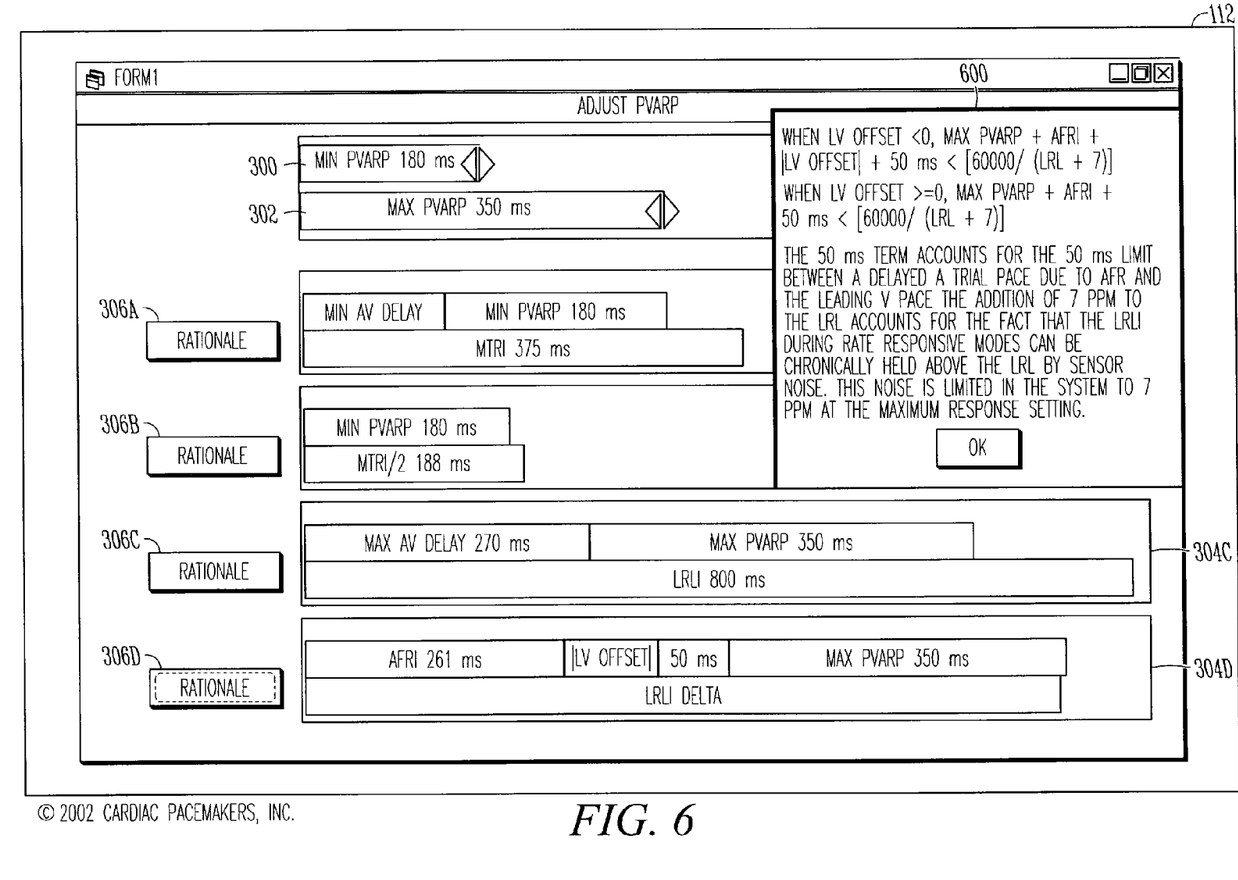
FIG. 6 illustrates the screen shot of FIG. 5 in which the display includes a further explanation of the flagged second rule violation.

In FIG. 3, display 112 also includes a "Rationale" button 306A–D corresponding to each graphical rule indication 304A–D. In response to the user clicking on the appropriate "Rationale" button, display 112 provides a box 600 that provides further textual or graphical information relating to that graphically-illustrated rule, as illustrated in the example of FIG. 6, for which the user has selected "Rationale" button 306D. By clicking on the "OK" button of box 600, display 112 discontinues its display of box 600.

Figure 7:
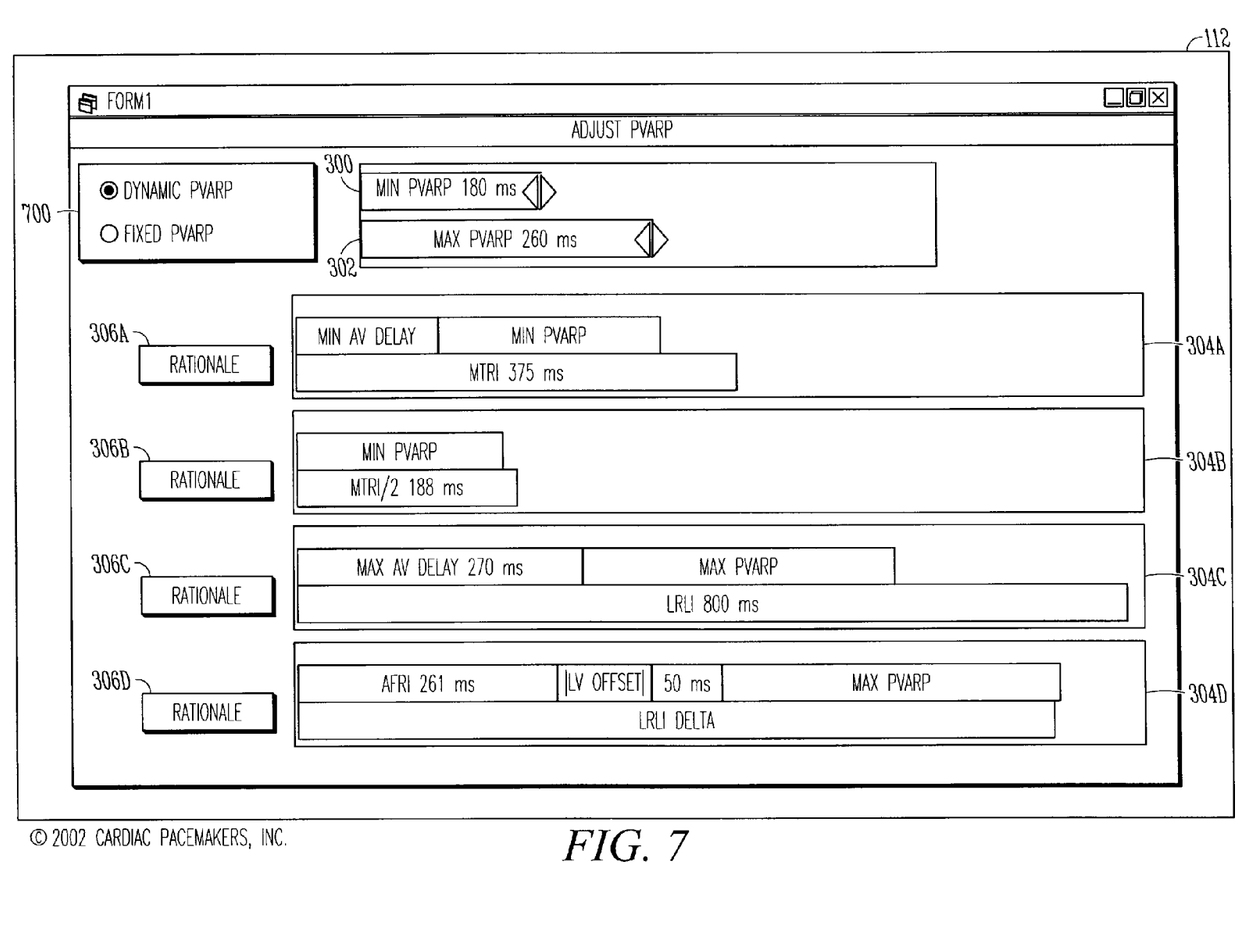
FIG. 7 is a screen shot of a portion of a display, similar to FIG. 3, but including a graphical parameter selector icon.

FIG. 7 is a screen shot of a portion of a display, similar to FIG. 3, but including a graphical parameter selector icon 700. Parameter selector icon 700 allows the user to select between different (related or unrelated) parameters, triggering a corresponding display of graphical illustrations of one or more rules associated with the selected parameter. In the example of FIG. 7, parameter selector icon 700 includes a button menu for selecting either "Dynamic PVARP" or "Fixed PVARP." In this example, the parameters "Dynamic PVARP" and "Fixed PVARP" are related in the sense that both apply to a PVARP, as discussed above. Unlike "Fixed PVARP," the value of the "Dynamic PVARP" parameter is a function of the patient's underlying heart rate and is, therefore, subject to an at least partially different set of rules governing the PVARP parameter. Patient selector icon 700 triggers display of graphical indications of the appropriate set of rules corresponding to the one of "Dynamic PVARP" and "Fixed PVARP" selector, and allows graphical adjustment of one or more parameters affected by the displayed rules.

Figure 8A:
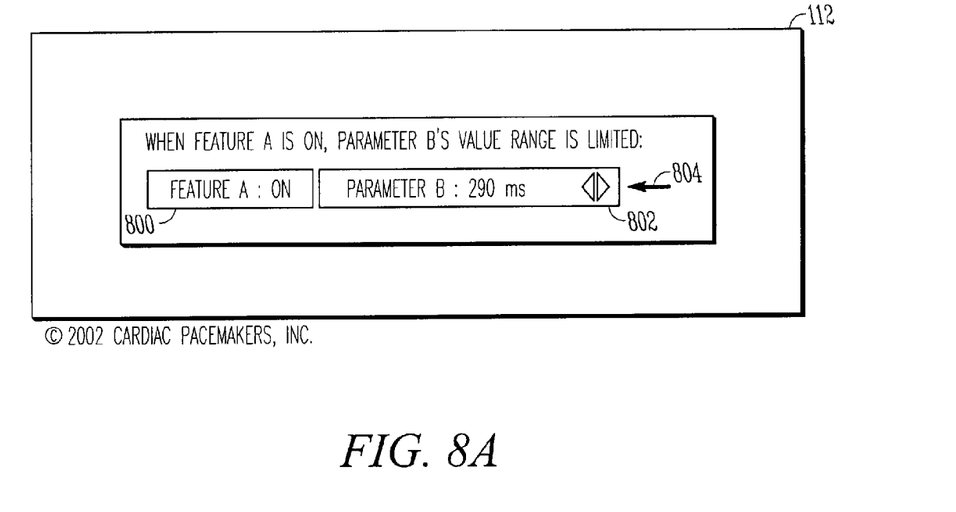
FIGS. 8A and 8B are screen shots of alternative portions of a display illustrating generally another embodiment of a rule-illustrative system and method for programmably adjusting at least one parameter of a device based on a value of a different parameter.
Figure 8B:
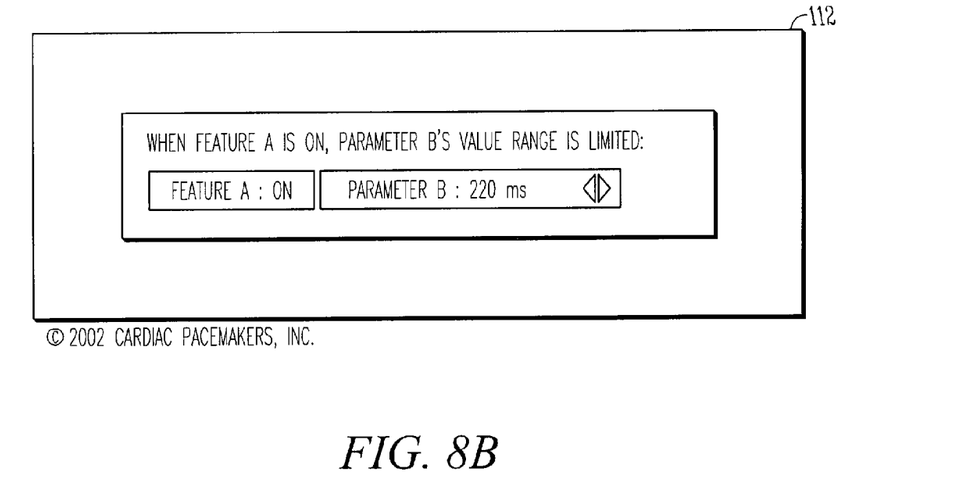

FIGS. 8A and 8B are screen shots of alternative portions of a display 112 that includes, by way of example, but not by way of limitation, another embodiment of a rule-illustrative system and method for programmably adjusting at least one parameter of a device 102 based on a value of a different parameter. FIG. 8A illustrates an example of a display 112 that includes at least two parameter icons. In this example, a first parameter icon 800 indicates graphically whether a binary-valued parameter, "Feature A," is on or off. A second parameter icon 802 indicates graphically a value of a range parameter, "Parameter B." In this example, icon 802 is a bar graph having a length that graphically indicates the value of "Parameter B" (the value is also indicated textually on icon 802). Icon 802 also allows the value of "Parameter B" to be adjusted by dragging an edge of the bar graph icon 802, such as discussed above. The displayed length of the bar graph icon 802 represents graphically to the user the value to which "Parameter B" is being programmed; in this example, the changing value is also indicated textually on bar graph icon 802.

FIG. 8A illustrates an example of a rule being violated. In one example, the rule violation triggers the illustrated textual description of the rule violation. In this case, when "Feature A" is "on," then the range of values to which "Parameter B" can be programmed is limited. Alternatively (or additionally), the occurrence of the rule violation is flagged graphically, such as by changing a background color, as discussed above. The example illustrated in FIG. 8A also includes a displayed corrective action indicator 804. In this example, the corrective action indicator 804 includes an arrow indicating the direction that the edge of bar graph icon 802 should be dragged to change the underlying value of "Parameter B" such that the rule is no longer violated; such a result is illustrated in FIG. 8B.

Figure 9A:
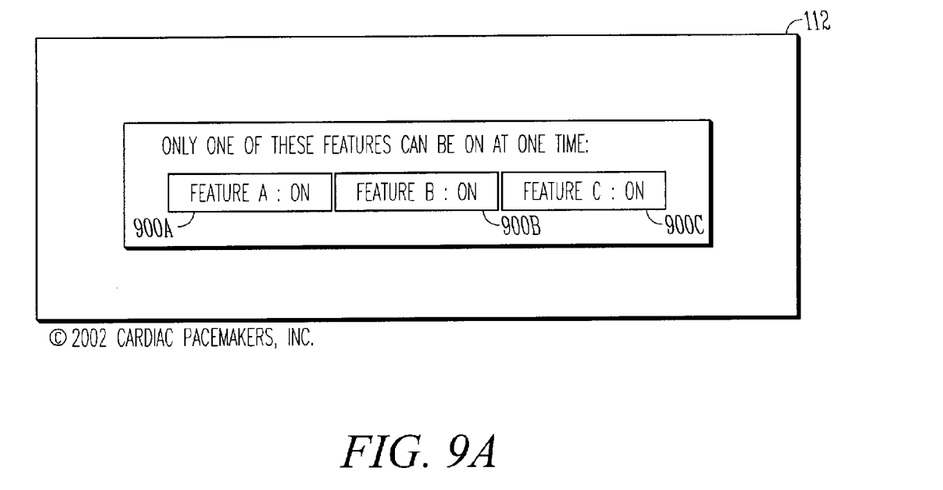
FIGS. 9A and 9B are screen shots of alternative portions of a display illustrating generally another embodiment of a rule-illustrative system and method for programmably adjusting at least one parameter of a device.
Figure 9B:
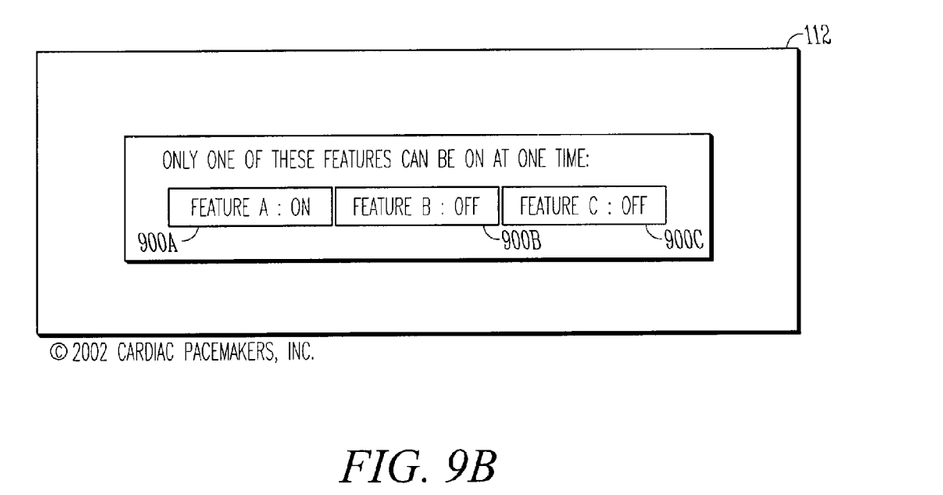

FIGS. 9A and 9B are screen shots of alternative portions of a display 112, including, by way of example, but not by way of limitation, another embodiment of a rule-illustrative system and method for programmably adjusting at least one parameter of a device 102. The example of FIG. 9A illustrates three parameter icons 900A, 900B, and 900C, respectively corresponding to the binary-valued (e.g., "on/off") parameters "Feature A," "Feature B," and "Feature C." In this example, a rule governing these three parameters indicates that only one of these "Feature A," "Feature B," and "Feature C" can be on at one time. Therefore, in this example, the three parameter icons 900A–C are presented in visual correspondence with each other, so that the user can easily determine how to resolve an underlying rule violation. In one example, the parameter icons 900A–C are displayed as user-selectable "buttons" that can be selected to toggle the value of the particular parameter corresponding to the icon between "on" and "off" to correct the rule violation; such a result is illustrated by the example of FIG. 9B. Moreover, in one example, a textual description of the underlying rule or rule violation is presented. In another example, a graphical indication flags rule violation, such as by a change in background color or other technique, as discussed above. In yet a further example, a graphical indication of corrective action is presented, such as, in this example, arrows pointing to the more than one feature that is "on" simultaneously in violation of the rule.

It is to be understood that the above description is intended to be illustrative, and not restrictive. For example, the above-discussed examples may be used in combination with each other. Many other embodiments will be apparent to those of skill in the art upon reviewing the above description. The scope of the invention should, therefore, be determined with reference to the appended claims, along with the full scope of equivalents to which such claims are entitled. Moreover, in the following claims, the terms "first,"

"second," "third," etc. are used merely as labels, and are not intended to impose numeric requirements on their objects.

What is claimed is:

1. A system comprising:
   a programmer device, including a communication circuit configured to be communicatively coupled to an implantable cardiac rhythm management (CRM) device, and including a user interface configured to program a plurality of parameters used by the CRM device, the user interface configured to interactively display, during a programming of at least one of the parameters:
      a graphical indication of a changing value of at least one of the parameters as at least one of the parameters is being programmed graphically; and
      a graphical illustration of how a rule constrains the value of the at least one of the parameters being programmed graphically.

2. The system of claim 1, in which the user interface is configured to interactively flag a violation of the rule constraining the at least one of the parameters being programmed as the value of the at least one of the parameters being programmed is being changed such that it violates the rule constraining the at least one of the parameters being programmed.

3. The system of claim 2, in which the user interface is configured to provide a corrective indication, if a violation of the rule is flagged, the corrective indication informing a user how the value of at least one parameter included by the rule should be changed to correct the violation of the rule.

4. The system of claim 1, in which the graphical indication of the changing value of the at least one parameter being programmed includes a draggable bar graph icon having a bar length indicative of the value of the at least one parameter being programmed.

5. The system of claim 4, in which the graphical indication of the rule includes a bar graph icon presented in visual correspondence with the graphical indication of the changing value of the at least one parameter being programmed.

6. The system of claim 1, in which the rule constraining the value of the at least one parameter being programmed includes a limit that constrains a combination of the value of the at least one parameter being programmed and a value of at least one other parameter.

7. The system of claim 1, in which the user interface includes a graphical indication of a changing value of the at least one parameter as it is being programmed together with a graphical indication of a plurality of rules constraining the value of the at least one parameter being programmed.

8. The system of claim 1, in which the user interface includes a graphical indication of a changing value of the at least one parameter as it is being programmed together with a graphical indication of every rule constraining the value of the at least one parameter being programmed.

9. The system of claim 1, in which the graphical indication of the rule constraining the value of the at least one parameter being programmed includes an accompanying icon that, when selected, triggers a textual display of a rationale underlying the rule constraining the value of the at least one parameter being programmed.

10. A system comprising:
    a programmer device, including a communication circuit configured to be communicatively coupled to an implantable cardiac rhythm management (CRM) device, and including a user interface configured to program a plurality of parameters used by the CRM device, the user interface interactively displaying, during a programming of at least one parameter, at least one graphical bar graph indication of a changing time interval value of the at least one parameter as it is being programmed together with a corresponding graphical illustration of how every applicable rule constrains the value of the at least one parameter being programmed.

11. The system of claim 10, in which at least one rule constraining the value of the at least one parameter being programmed includes a limit that constrains a combination of the value of the at least one parameter being programmed and a value of at least one other parameter.

12. A method of programming an implantable cardiac rhythm management device, the method comprising:
    providing to a user a graphical indication of a value of a first parameter being programmed graphically by the user, the graphical indication being modifiable by the user to program the value of the first parameter; and
    providing to the user a graphical illustration of how a rule constrains the value of the first parameter being programmed graphically by the user.

13. The method of claim 12, further comprising flagging a violation of the rule constraining the first parameter being programmed as the value of the first parameter being programmed is being changed such that it violates the rule constraining the first parameter being programmed.

14. The method of claim 13, further comprising providing a corrective indication, upon the flagging the violation of the rule, the corrective indication informing a user how the value of the first parameter should be changed to correct the violation of the rule.

15. The method of claim 12, in which the providing to the user the graphical indication of the value of the first parameter being programmed includes providing a draggable bar graph icon having a bar length indicative of the value of the first parameter.

16. The method of claim 15, in which the providing to the user the graphical indication of the rule includes providing a bar graph icon presented in visual correspondence with the graphical indication of the value of the first parameter.

17. The method of claim 12, in which the providing to the user the graphical indication of the rule includes providing a limit that constrains a combination of the value of the first parameter being programmed and a value of at least one other parameter.

18. The method of claim 12, further comprising providing to the user a graphical indication of a changing value of the first parameter as it is being programmed together with a graphical indication of a plurality of rules constraining the value of the first parameter being programmed.

19. The method of claim 12, further comprising providing to the user a graphical indication of a changing value of the first parameter as it is being programmed together with a graphical indication of every rule constraining the value of the first parameter being programmed.

20. The method of claim 12, in which the providing to the user a graphical indication of the rule constraining the value of the first parameter being programmed further comprises providing an accompanying icon that, when selected by the user, triggers a textual display of the rationale underlying the rule constraining the value of the first parameter being programmed.

21. A system comprising:
    a programmer device, including a communication circuit configured to be communicatively coupled to an implantable cardiac rhythm management (CRM) device, and including a user interface configured to program a plurality of parameters used by the CRM device, the user interface interactively displaying together, during a programming of at least one parameter, a plurality of graphical icons corresponding to respective binary-valued parameters and an indication of how a rule limits the number of the parameters that can concurrently be programmed to a particular binary-valued state.

22. The system of claim 21, in which the user interface is configured to interactively graphically flag a violation of the rule.

23. The system of claim 22, in which the user interface is configured to provide a corrective indication, if a violation of the rule is flagged, the corrective indication informing a user how the value of at least one parameter governed by the rule should be changed to correct the violation of the rule.

24. A method of programming an implantable cardiac rhythm management device, the method comprising:
  displaying to a user, in visual correspondence, graphical icons corresponding to binary-valued parameters and an indication of how a rule limits the number of the parameters that can concurrently be programmed to a particular binary-valued state, each icon being selectable to program the parameter corresponding to that icon; and
  receiving from the user a selection of one of the icons to program the corresponding parameter to a particular binary-valued state.

25. The method of claim 24, further comprising graphically flagging a violation of the rule.

26. The method of claim 24, further comprising providing a graphical corrective action indication, if a violation of the rule exists, the corrective indication informing a user how to correct the violation of the rule.

27. A system comprising:
  a programmer device, including a communication circuit configured to be communicatively coupled to an implantable cardiac rhythm management (CRM) device, and including a user interface configured to program a plurality of parameters used by the CRM device, the user interface configured to interactively display, during a programming of at least one of the parameters:
    means for graphically changing value of at least one of the parameters as at least one of the parameters is being programmed graphically; and
    a graphical illustration of how a rule constrains the value of the at least one of the parameters being programmed graphically.

28. The system of claim 27, in which the user interface is configured to interactively flag a violation of the rule constraining the at least one of the parameters being programmed as the value of the at least one of the parameters being programmed is being changed such that it violates the rule constraining the at least one of the parameters being programmed.

29. The system of claim 28, in which the user interface is configured to provide a corrective indication, if a violation of the rule is flagged, the corrective indication informing a user how the value of at least one parameter included by the rule should be changed to correct the violation of the rule.

* * * * *